(12) United States Patent
Muraca

(10) Patent No.: US 9,056,919 B2
(45) Date of Patent: Jun. 16, 2015

(54) USP2A PEPTIDES AND ANTIBODIES

(71) Applicant: Nuclea Biotechnologies, Inc., Pittsfield, MA (US)

(72) Inventor: Patrick J. Muraca, Pittsfield, MA (US)

(73) Assignee: NUCLEA BIOTECHNOLOGIES, INC., Pittsfield, MA (US)

( * ) Notice: Subject to any disclaimer, the term of this patent is extended or adjusted under 35 U.S.C. 154(b) by 0 days.

(21) Appl. No.: 13/659,173

(22) Filed: Oct. 24, 2012

(65) Prior Publication Data
US 2013/0109587 A1 May 2, 2013

Related U.S. Application Data

(60) Provisional application No. 61/551,567, filed on Oct. 26, 2011.

(51) Int. Cl.
| | |
|---|---|
| *G01N 33/573* | (2006.01) |
| *C07K 14/47* | (2006.01) |
| *C07K 16/40* | (2006.01) |
| *C12N 9/64* | (2006.01) |
| *G01N 33/574* | (2006.01) |
| *C12Q 1/68* | (2006.01) |
| *G01N 33/68* | (2006.01) |
| *C12Q 1/37* | (2006.01) |
| *C07K 7/08* | (2006.01) |

(52) U.S. Cl.
CPC ............... *C07K 14/47* (2013.01); *C07K 16/40* (2013.01); *C12N 9/6421* (2013.01); *G01N 33/573* (2013.01); *G01N 33/574* (2013.01); *G01N 33/57434* (2013.01); *C07K 2317/34* (2013.01); *C12Q 1/6886* (2013.01); *G01N 33/6854* (2013.01); *C12Q 1/37* (2013.01); *G01N 2800/52* (2013.01); *G01N 2800/56* (2013.01); *C07K 7/08* (2013.01); *C12N 9/6472* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2004/0053269 A1* | 3/2004 | Todd et al. | 435/6 |
| 2005/0196754 A1 | 9/2005 | Drmanac et al. | |
| 2008/0050278 A1 | 2/2008 | Farina et al. | |

FOREIGN PATENT DOCUMENTS

| | | |
|---|---|---|
| WO | 0220736 | 3/2002 |

OTHER PUBLICATIONS

Graner et al (2004) "The isopeptidase USP2a regulates the stability of fatty acid synthase in prostate cancer" Cancer Cell 5(3)253-261.*
Aviva Systems Biology (www.avivasysbio.com) product data sheet for ARP59312-P050 (2011).*
Graner, et al. "The isopeptidase USP2a regulates the stability of fatty acid synthase in prostate cancer." Cancer Cell: Mar. 2004, vol. 5. pp. 253-261.
Priolo et al. "The Isopeptidase USP2a Protexts Human Prostate Cancer from Apoptosis" Cancer Res 2006; 66:(17). Sep. 1, 2006. pp. 8625-8632.
International Search Report for International Application No. PCT/US2012/061543, dated Feb. 8, 2013.

* cited by examiner

*Primary Examiner* — Tracy Vivlemore
*Assistant Examiner* — Karen S Weiler
(74) *Attorney, Agent, or Firm* — Donna T. Ward; Lingyun Jia; DT Ward, PC

(57) ABSTRACT

The invention relates to novel USP2a peptides and antibodies, as well as nucleic acids related to them. The peptides, antibodies and the nucleic acids are useful for the detection, staging and monitoring of the progression of cancer, as well as for determining or monitoring the efficacy of treatment.

5 Claims, No Drawings

SEQUENCE LISTING

<160> NUMBER OF SEQ ID NOS: 3

<210> SEQ ID NO 1
<211> LENGTH: 21
<212> TYPE: PRT
<213> ORGANISM: Homo sapiens

<400> SEQUENCE: 1

Leu Thr Arg Pro Arg Thr Tyr Gly Pro Ser Ser Leu Leu Asp Tyr
1               5                   10                  15

Asp Arg Gly Arg Pro Leu
                20

<210> SEQ ID NO 2
<211> LENGTH: 19
<212> TYPE: PRT
<213> ORGANISM: Homo sapiens

<400> SEQUENCE: 2

Gly Gly Gly Lys Arg Ala Glu Ser Gln Thr Arg Gly Thr Glu Arg
1               5                   10                  15

Pro Leu Gly Ser

<210> SEQ ID NO 3
<211> LENGTH: 3748
<212> TYPE: DNA
<213> ORGANISM: Homo sapiens
<220> FEATURE:
<221> NAME/KEY: CDS
<222> LOCATION: (296)..(2113)

<400> SEQUENCE: 3
agtgacgcga gacgcggggt gtggctctgc cggcccaggc gcgatgaggc ggctgcccgc      60
tgggtggcgc cgatttcccg gggaggtccc ttctgggccc ccggcggagg tgggagagag    120
tcaggcagga gccgaggccg gggagccctc ttcgtcagct ggtgctcact gcgccgcgcc    180
agcgccagcc gggactcacc cgcagctcca tgcttgtgcc cggttcgact cgtccatact    240

| | |
|---|---|
| ccaagaagag gcagcccatg aggctcccag tccccactga gtgccaccct gaagg atg<br>                                                                                                         Met<br>                                                                                                          1 | 298 |
| tcc cag ctc tcc tcc acc ctg aag cgc tac aca gaa tcg gcc cgc tac<br>Ser Gln Leu Ser Ser Thr Leu Lys Arg Tyr Thr Glu Ser Ala Arg Tyr<br>              5                      10                        15 | 346 |
| aca gat gcc cac tat gcc aag tcg ggc tat ggt gcc tac acc ccg tcc<br>Thr Asp Ala His Tyr Ala Lys Ser Gly Tyr Gly Ala Tyr Thr Pro Ser<br>          20                      25                        30 | 394 |
| tcc tat ggg gcc aat ctg gct gcc tcc tta ctg gag aag gag aaa ctt<br>Ser Tyr Gly Ala Asn Leu Ala Ala Ser Leu Leu Glu Lys Glu Lys Leu<br> 35                        40                        45 | 442 |
| ggt ttc aag ccg gtc ccc acc agc agc ttc ctc acc cgt ccc cgt acc<br>Gly Phe Lys Pro Val Pro Thr Ser Ser Phe Leu Thr Arg Pro Arg Thr<br>50                    55                        60                        65 | 490 |
| tat ggc ccc tcc tcc ctc ctg gac tat gac cgg ggc cgc ccc ctg ctg<br>Tyr Gly Pro Ser Ser Leu Leu Asp Tyr Asp Arg Gly Arg Pro Leu Leu<br>                    70                        75                        80 | 538 |
| aga ccc gac atc act ggg ggt ggt aag cgg gca gag agc cag acc cgg<br>Arg Pro Asp Ile Thr Gly Gly Gly Lys Arg Ala Glu Ser Gln Thr Arg<br>              85                      90                        95 | 586 |
| ggt act gag cgg cct tta ggc agt ggc ctc agc ggg ggc agc gga ttc<br>Gly Thr Glu Arg Pro Leu Gly Ser Gly Leu Ser Gly Gly Ser Gly Phe<br>          100                      105                      110 | 634 |
| cct tat gga gtg acc aac aac tgc ctc agc tac ctg ccc atc aat gcc<br>Pro Tyr Gly Val Thr Asn Asn Cys Leu Ser Tyr Leu Pro Ile Asn Ala<br>115                    120                      125 | 682 |
| tat gac cag ggg gtg acc cta acc cag aag ctg gac agc caa tca gac<br>Tyr Asp Gln Gly Val Thr Leu Thr Gln Lys Leu Asp Ser Gln Ser Asp<br>130                    135                      140                    145 | 730 |
| ctg gcc cgg gat ttc tcc agc ctc cgg acc tca gat agc tac cgg ata<br>Leu Ala Arg Asp Phe Ser Ser Leu Arg Thr Ser Asp Ser Tyr Arg Ile<br>                    150                      155                    160 | 778 |
| gac ccc agg aac ctg ggc cgc agc ccc atg ctg gcc cgg acg cgc aag<br>Asp Pro Arg Asn Leu Gly Arg Ser Pro Met Leu Ala Arg Thr Arg Lys<br>          165                      170                      175 | 826 |
| gag ctc tgc acc ctg cag ggg ctc tac cag aca gcc agc tgc cct gaa<br>Glu Leu Cys Thr Leu Gln Gly Leu Tyr Gln Thr Ala Ser Cys Pro Glu<br>              180                      185                    190 | 874 |
| tac ctg gtc gac tac ctg gag aac tat ggt cgc aag ggc agt gca tct<br>Tyr Leu Val Asp Tyr Leu Glu Asn Tyr Gly Arg Lys Gly Ser Ala Ser<br>195                    200                      205 | 922 |
| cag gtg ccc tcc cag gcc cct ccc tca cga gtc cct gaa atc atc agc<br>Gln Val Pro Ser Gln Ala Pro Pro Ser Arg Val Pro Glu Ile Ile Ser<br>210                    215                      220                    225 | 970 |
| cca acc tac cga ccc att ggc cgc tac acg ctg tgg gag acg gga aag<br>Pro Thr Tyr Arg Pro Ile Gly Arg Tyr Thr Leu Trp Glu Thr Gly Lys<br>                    230                      235                    240 | 1018 |
| ggt cag gcc cct ggg ccc agc cgc tcc agc tcc ccg gga aga gac ggc<br>Gly Gln Ala Pro Gly Pro Ser Arg Ser Ser Ser Pro Gly Arg Asp Gly<br>          245                      250                      255 | 1066 |
| atg aat tct aag agt gcc cag ggt ctg gct ggt ctt cga aac ctt ggg<br>Met Asn Ser Lys Ser Ala Gln Gly Leu Ala Gly Leu Arg Asn Leu Gly<br>              260                      265                    270 | 1114 |
| aac acg tgc ttc atg aac tca att ctg cag tgc ctg agc aac act cgg<br>Asn Thr Cys Phe Met Asn Ser Ile Leu Gln Cys Leu Ser Asn Thr Arg<br>275                    280                      285 | 1162 |
| gag ttg aga gat tac tgc ctc cag agg ctc tac atg cgg gac ctg cac<br>Glu Leu Arg Asp Tyr Cys Leu Gln Arg Leu Tyr Met Arg Asp Leu His<br>290                    295                      300                    305 | 1210 |

-continued

```
cac ggc agc aat gca cac aca gcc ctc gtg gaa gag ttt gca aaa cta    1258
His Gly Ser Asn Ala His Thr Ala Leu Val Glu Glu Phe Ala Lys Leu
            310                 315                 320 att cag acc ata tgg act tca tcc ccc aat gat gtg gtg agc cca tct    1306
Ile Gln Thr Ile Trp Thr Ser Ser Pro Asn Asp Val Val Ser Pro Ser
        325                 330                 335 gag ttc aag acc cag atc cag aga tac gca ccg cgc ttt gtt ggc tat    1354
Glu Phe Lys Thr Gln Ile Gln Arg Tyr Ala Pro Arg Phe Val Gly Tyr
            340                 345                 350 aat cag cag gat gct cag gag ttc ctt cgc ttt ctt ctg gat ggg ctc    1402
Asn Gln Gln Asp Ala Gln Glu Phe Leu Arg Phe Leu Leu Asp Gly Leu
        355                 360                 365 cat aac gag gtg aac cga gtg aca ctg aga cct aag tcc aac cct gag    1450
His Asn Glu Val Asn Arg Val Thr Leu Arg Pro Lys Ser Asn Pro Glu
370                 375                 380                 385 aac ctc gat cat ctt cct gat gac gag aaa ggc cga cag atg tgg aga    1498
Asn Leu Asp His Leu Pro Asp Asp Glu Lys Gly Arg Gln Met Trp Arg
            390                 395                 400 aaa tat cta gaa cgg gaa gac agt agg atc ggg gat ctc ttt gtt ggg    1546
Lys Tyr Leu Glu Arg Glu Asp Ser Arg Ile Gly Asp Leu Phe Val Gly
        405                 410                 415 cag cta aag agc tcg ctg acg tgt aca gat tgt ggt tac tgt tct acg    1594
Gln Leu Lys Ser Ser Leu Thr Cys Thr Asp Cys Gly Tyr Cys Ser Thr
            420                 425                 430 gtc ttc gac ccc ttc tgg gac ctc tca ctg ccc att gct aag cga ggt    1642
Val Phe Asp Pro Phe Trp Asp Leu Ser Leu Pro Ile Ala Lys Arg Gly
        435                 440                 445 tat cct gag gtg aca tta atg gac tgc atg agg ctc ttc acc aaa gag    1690
Tyr Pro Glu Val Thr Leu Met Asp Cys Met Arg Leu Phe Thr Lys Glu
450                 455                 460                 465 gat gtg ctt gat gga gat gaa aag cca aca tgc tgt cgc tgc cga ggc    1738
Asp Val Leu Asp Gly Asp Glu Lys Pro Thr Cys Cys Arg Cys Arg Gly
            470                 475                 480 aga aaa cgg tgt ata aag aag ttc tcc atc cag agg ttc cca aag atc    1786
Arg Lys Arg Cys Ile Lys Lys Phe Ser Ile Gln Arg Phe Pro Lys Ile
        485                 490                 495 ttg gtg ctc cat ctg aag cgg ttc tca gaa tcc agg atc cga acc agc    1834
Leu Val Leu His Leu Lys Arg Phe Ser Glu Ser Arg Ile Arg Thr Ser
            500                 505                 510 aag ctc aca aca ttt gtg aac ttc ccc cta aga gac ctg gac tta aga    1882
Lys Leu Thr Thr Phe Val Asn Phe Pro Leu Arg Asp Leu Asp Leu Arg
        515                 520                 525 gaa ttt gcc tca gaa aac acc aac cat gct gtt tac aac ctg tac gct    1930
Glu Phe Ala Ser Glu Asn Thr Asn His Ala Val Tyr Asn Leu Tyr Ala
530                 535                 540                 545 gtg tcc aat cac tcc gga acc acc atg ggt ggc cac tat aca gcc tac    1978
Val Ser Asn His Ser Gly Thr Thr Met Gly Gly His Tyr Thr Ala Tyr
            550                 555                 560 tgt cgc agt cca ggg aca gga gaa tgg cac act ttc aac gac tcc agc    2026
Cys Arg Ser Pro Gly Thr Gly Glu Trp His Thr Phe Asn Asp Ser Ser
        565                 570                 575 gtc act ccc atg tcc tcc agc caa gtg cgc acc agc gac gcc tac ctg    2074
Val Thr Pro Met Ser Ser Ser Gln Val Arg Thr Ser Asp Ala Tyr Leu
            580                 585                 590 ctc ttc tac gaa ctg gcc agc ccg ccc tcc cga atg tag cgccaggagc    2123
Leu Phe Tyr Glu Leu Ala Ser Pro Pro Ser Arg Met
        595                 600                 605
```

```
cacgtccctt ctcccttccc cgtggtggcc ccgctcccta aatttttaa aaagacaaaa    2183 acaaaacaac aacaacaaca cacaaacctg acaagagaaa aacaaacctg aagctgccga    2243
gcaggagtgg atgcagcctg atcagggtct ggagcaagga gccgggcttt cctgagctgt    2303
ggcccggcag ggaagatcgc ctggacgtgg agccagcatc gccccgtgcc ctcggcgttt    2363
gcatttgtaa acttgtggtc ttcctatgtg tcagaaacaa ctgtgtcttg gggggaaga     2423 ccctcgctgc gccgcttccc gccgcagcgc ccgcgcctcc gaggggacag cgccctctgg    2483
agctcgctgg gagcatcacc gcctggacgc ccgcgccgcg gaggagccgg cgcccatctc    2543
cacccgcacg gctcgccggt ccagagccat gagccaagag ccctcttcac gctgctaact    2603 ccagggggaca gacgaaggga catctttgga aaacgctggt tttggttttt aaaaagccca   2663
actttttttt tttaatttcc ataactaaag tgttcagact ggagtgctct ccttcaggcc    2723
tcttcatagc tgggacgttg cactggtcct tttattgctt ttccaagtac aactttctaa    2783
tgctagccct ccgtggtgct aggtgggcgt tggccaggcc ccaagcacag ccacagtaga    2843
cctgggatct aaaacaagtt tctgttttgg gggtttgggt tttttttttt ttttttaat    2903 gttttgaatg gaatttagtt gcctccaaga attgtgcctt atagcatttg gggaccaggg    2963
ggtaactgcc cctcctgaaa tatccctcag cctcttccct tttccccagt gctctgttca    3023
aacccgcctg ggaaagggat cctgcccta gccctggctc gttgtgcatt gcagtgaggc     3083
aaagaagaaa gcaggtagat tccttccgac agggcatcaa gttcttcccg cccacgtcct    3143
ctagcccacc cctggtctgc tccccagctg tttgaaggat agcacaagcc cctcgtccct    3203
agagcttctc tccctttttat ttattctctt aacatccctt tccccctggc cttcctgccc   3263
ccgccccctt ctcagagcct cctagacaat aggccctttg gaccgagttt ctcagggatg    3323
cccaggccac ccctcagctc ttcttagcgc tggtctccag tcctgccctg ggagctggag    3383
cctgggtatt tggggacatc ttgcctcagt tgtatggttc tttcctgtgg gctcaatttt    3443
gccctacata gttggataaa actctgtgct gtcctggaga gtaaagctgt tcacccacac    3503
agctgggccc ggcttgtgcc ccgtggagcc tggcacattc caggctccta ggaggaggca    3563
tcagagaaag acaccctgag ttttactggc ctgacaccct tctccagaga agacctgtga    3623
acctgagccc aagggcaagt gtacacttgt ttactgtgta agcaagagta gaagaatgtc    3683
taatgtacag tggaaccttg tacagaataa ataatagctt tgagaaatca aaaaaaaaa    3743 aaaaa                                                              3748
```

USP2A PEPTIDES AND ANTIBODIES

CROSS REFERENCE TO RELATED APPLICATIONS

This application claims priority to U.S. Provisional Patent Application No. 61/551,567 filed Oct. 26, 2011 which is incorporated by reference in its entirety.

REFERENCE TO SEQUENCE LISTING

The present application is being filed along with a Sequence Listing in electronic format. The Sequence Listing is provided as a file entitled 20151007USSEQLST.txt, created on Oct. 24, 2012 which is 12,323 bytes in size. The information in the electronic format of the sequence listing is incorporated herein by reference in its entirety.

FIELD OF INVENTION

The invention relates to peptides and antibodies having immunospecificity for USP2a polypeptides and proteins, as well as nucleic acids related to these peptides and antibodies, and methods for using these peptides and antibodies.

BACKGROUND OF THE INVENTION

According to the American Cancer Society, in 2009 there were over 190,000 cases of prostate cancer reported and over 27,000 related deaths in the United States.

The ubiquitin-specific protease 2a (USP2a) can deubiquitinate the antiapoptotic proteins fatty acid synthase (FAS) and Mdm2. It has been shown that when USP2a is also overexpressed in nontransformed cells, it exhibits oncogenic behavior both in vitro and in vivo and also prevents apoptosis induced by chemotherapeutic agents. Notably, USP2a silencing in several human cancer cell lines can result in apoptosis.

USP2a is overexpressed in about 50% of human prostate tumors, and its oncogenicity in prostate cancer as well as its anti-apoptotic role in a variety of human tumor cell lines have been thoroughly demonstrated, making USP2a a good therapeutic target and prognostic marker in human cancer. However, currently available anti-USP2a antibodies are not specific enough and therefore are likely to cross-react with other proteins. This lack of specificity renders the current anti-USP2a antibodies less useful in both therapeutic discovery and as a marker in the analysis of patient tumors. Consequently, there remains a need for better USP2a antibodies useful in the diagnosis, stratification and prognosis of disorders and conditions, especially cancers.

SUMMARY OF THE INVENTION

The present invention provides peptides and antibodies having immunospecificity for USP2a polypeptides and proteins. The present invention further provides nucleic acids related to these peptides and antibodies. The present invention also provides diagnostic and therapeutic compositions and methods using these peptides, antibodies and nucleic acids.

In one embodiment, the present invention provides an isolated and/or recombinant USP2a peptide comprising an amino acid sequence selected from the group consisting of SEQ ID NO. 1, SEQ ID NO. 2 and variants thereof.

In a further embodiment, the present invention provides antibodies specifically immunoreactive with one or more peptides comprising an amino acid sequence selected from the group consisting of SEQ ID NO. 1, SEQ ID NO 2, and variants thereof.

In one embodiment, the present invention provides an isolated nucleic acid molecule comprising a sequence encoding a peptide selected from the group consisting of SEQ ID NO. 1, SEQ ID NO. 2 and variants thereof.

In a further embodiment, the USP2a peptide, antibody, or nucleic acid of the present invention may further comprise a detectable label. The USP2a peptide, antibody, or nucleic acid of the present invention may be immobilized on a substrate.

In one embodiment, the present invention provides a composition for detecting USP2a polypeptides or proteins in a sample which comprises a primary antibody specifically immunoreactive with a USP2a peptide comprising an amino acid sequence selected from the group consisting of SEQ ID NO. 1, SEQ ID NO. 2 and variants thereof. In a further embodiment, the primary antibody may be labeled with a detectable label.

In one embodiment, the composition of the present invention may further comprise a secondary antibody. In a further embodiment, the secondary antibody may react with the primary antibody. In another embodiment, the secondary antibody is specifically immunoreactive with a USP2a peptide comprising an amino acid sequence selected from the group consisting of SEQ ID NO. 1, SEQ ID NO. 2 and variants thereof. In a further embodiment, the secondary antibody may be labeled with a detectable label.

In one embodiment, the present invention provides a composition for detecting one or more USP2a polypeptides or proteins in a sample, comprising a nucleic acid which comprises at least a portion of a sequence encoding a peptide selected from the group consisting of SEQ ID NO. 1, SEQ ID NO. 2 and variants thereof. In a further embodiment, the nucleic acid preferably comprises at least from about 5 up to about 80 nucleic acid bases encoding all or a portion of a peptide selected from the group consisting of SEQ ID NO. 1, SEQ ID NO. 2 and variants thereof. In another embodiment, the nucleic acid may be labeled with a detectable label.

In one embodiment, the present invention provides a method for detecting, diagnosing, staging or monitoring the progression of a disease in a subject, where the method comprises: a) obtaining a sample from the subject, b) contacting the sample with an antibody specifically immunoreactive with a USP2a peptide comprising an amino acid sequence selected from the group consisting of SEQ ID NO. 1, SEQ ID NO. 2 and variants thereof, c) determining a level of USP2a protein in the sample detected by said antibody, and d) comparing the level of the USP2a protein in the sample to a baseline level of the USP2a protein; where a difference in levels of the USP2a protein in the sample as compared to a baseline of greater than 1%, 5%, 50%, 75%, 100% or more is indicative of the presence, stage or progression of the disease in the subject. In a further embodiment the disease may be cancer.

In a further embodiment, the detection of the USP2a protein may be accomplished using any type of immunoassay, for example, an immunoassay selected from immunoblot assay, enzyme-linked immunosorbant assay (ELISA), radioimmunoassay (RIA), immunoprecipitation, immunohistochemistry (IHC) or immunofluorescence.

In one embodiment, the present invention provides a method for detecting, diagnosing, staging or monitoring the progression of a USP2a disease or condition in a subject, where the method comprises: a) obtaining a sample from the subject, b) contacting the sample with an nucleic specifically immunoreactive with a USP2a nucleic acid comprising an amino acid sequence selected from the group consisting of SEQ ID NO. 1, SEQ ID NO. 2 and variants thereof, c) determining a level of USP2a nucleic acid in the sample detected by said nucleic acid, and d) comparing the level of the USP2a nucleic acid in the sample to a baseline level of the USP2a nucleic acid; where a difference in levels of the USP2a nucleic acid in the sample as compared to a baseline of greater than 1%, 5%, 50%, 75%, 100% or more is indicative of the presence, stage or progression of the USP2a-mediated disease in the subject.

In a further embodiment, the USP2a nucleic acid may be a DNA or an RNA. In further embodiment, the present invention provides a method further comprising determining the efficacy of therapeutic intervention or treatment by a step of modifying therapeutic intervention or treatment of the USP2a disease or condition based on the difference in USP2a levels.

In a further embodiment, the detection of USP2a nucleic acid may be accomplished by a method selected from the group consisting of polymerase chain reaction (PCR), reverse transcriptase-PCR (RT-PCR), in situ hybridization, Southern blot, Northern blot, sequence analysis, gene microarray analysis, and detection of a reporter gene.

In one embodiment, the provided sample is obtained from a patient to be diagnosed, monitored or treated for the disease, and the baseline level is from a control sample from a patient not having the disease.

In another embodiment, the sample is from a subject who is known to have the disease, and the baseline level comprises a level of USP2a from a previous sample from the same subject, wherein a difference in the level of the USP2a indicates that the subject is at a different disease stage, or is indicative of the efficacy of therapeutic intervention or treatment, e.g., the responsiveness of the patient to therapy.

In a further embodiment, the sample of the invention may comprise, for example, a bodily fluid sample, a tissue sample, or a cell sample. In a further embodiment, the sample may be immobilized on a substrate.

In one embodiment, the method of the present invention is used to determine the prognosis of the disease in a patient. In another embodiment, the method of the present invention is used to determine the susceptibility of a patient to a therapeutic treatment.

In one embodiment, the present invention provides for an antibody obtained by the method which comprises the steps of: a) contacting a subject with at least one USP2a peptide comprising a portion of a USP2a protein, wherein the USP2a peptide is from about 5 to about 30 amino acids in length and has a sequence selected from the group consisting of SEQ ID NO. 1, SEQ ID NO. 2 and variants thereof, and b) collecting a sample containing the USP2a antibody from the subject. In a further embodiment, the sample collected contains antiserum that has been immunopurified.

In another embodiment, the antibody created by the method of the present invention is a monoclonal antibody. In a further embodiment, the antibody created by the method of the present invention contains a detectable label.

In one embodiment, the present invention provides a method for detecting the presence or amount of USP2a protein in a sample comprising contacting the sample with the isolated antibody of the present invention.

In one embodiment, the present invention also provides an expression vector comprising a nucleic acid which comprises a sequence encoding a peptide selected from the group consisting of SEQ ID NO. 1, SEQ ID NO. 2, and variants thereof. In a further embodiment, the present invention provides a host cell transfected with the expression vector.

DETAILED DESCRIPTION OF THE INVENTION

The invention relates to peptides and antibodies having immunospecificity for USP2a peptides and proteins, as well as nucleic acids related to these peptides and antibodies, and methods for using these peptides and antibodies.

Unless otherwise defined, all technical and scientific terms used herein have the same meaning as commonly understood by one of ordinary skill in the art to which this invention belongs. Although methods and materials similar or equivalent to those described herein can be used in the practice or testing of methods featured in the invention, suitable methods and materials are described below.

Definitions

For convenience, the meaning of certain terms and phrases employed in the specification, examples, and appended claims are provided below. The definitions are not meant to be limiting in nature and serve to provide a clearer understanding of certain aspects of the present invention.

The term "peptide" refers to a natural or synthetic molecule comprising two or more amino acids linked by the carboxyl group of one amino acid and the amino group of another. A peptide of the present invention is not limited by length, thus the term encompasses polypeptide and protein. A "USP2a peptide" of the present invention is a peptide fragment derived from a USP2a protein and is preferably between about 2 to about 100 amino acids in length, more preferably between about 5 to about 50 amino acids in length, more preferably between about 10 to about 30 amino acids in length, even more preferably between about 10 to about 20 amino acids in length. The terms polypeptide and protein sometimes are used interchangeably. A "USP2a polypeptide" or "USP2a protein" may refer to an entire USP2a protein (SEQ ID NO. 3), or to fragment or variant thereof. A "fragment," as used herein, refers to a polypeptide or protein that is a portion of another polypeptide or protein. For example, fragments of proteins may comprise polypeptides obtained by digesting full-length protein isolated from cultured cells. As used herein, a "variant" of a peptide or protein is defined as one which is at least the functional equivalent of the parent molecule but which may differ in sequence by no more than 20% in sequence from the parent molecule.

The term "immunogenic epitope" refers to a portion of a peptide that elicits an antibody response in an animal, as determined by any method known in the art, for example, by the methods for generating antibodies described herein. (See, for example, Geysen et al., 1983, Proc. Natl. Acad. Sci. USA, 81:3998-4002). The term "antigenic epitope" refers to a portion of a protein to which an antibody can immunospecifically bind to its antigen as determined by any method well known in the art, for example, by the immunoassays described herein. Antigenic epitopes need not necessarily be immunogenic. Peptides that function as epitopes may be produced by any conventional means. (See, e.g., Houghten, 1985, Proc. Natl. Acad. Sci. USA, 82:5131-5135; and as described in U.S. Pat. No. 4,631,211).

The term "isolated," with respect to peptides, nucleic acids, or antibodies, refers to the material that is removed from its original environment (e.g., the natural environment if it is naturally occurring material). For example, a naturally-occurring nucleic acid or peptide or antibody present in a living animal is not isolated, but the same nucleic acid or peptide or antibody, which is separated from some or all of the coexisting materials in the natural system, is isolated. Such isolated nucleic acid could be part of a vector and such isolated nucleic acid or peptide or antibody could be part of a composition, and still be isolated in that the vector or composition is not part of its natural environment. An "isolated" peptide, nucleic acid or antibody, also includes material synthesized, or produced by recombinant DNA technology, as well as preparations such as serum containing an antibody of the invention.

The term "specifically immunoreactive," as used herein, refers to a measurable and reproducible specific immunoreaction such as binding between a peptide and an antibody, that is determinative of the presence of the peptide in the presence of a heterogeneous population of peptides and other biologics. The term specifically immunoreactive may include specific recognition of structural shapes and surface features. Thus, under designated conditions, an antibody specifically immunoreactive to a particular peptide will not significantly bind to other peptides present in the sample. An antibody specifically immunoreactive to a peptide has an association constant of at least $10^3 M^{-1}$ or $10^4 M^{-1}$, sometimes about $10^5 M^{-1}$ or $10^6 M^{-1}$, in other instances $10^6 M^{-1}$ or $10^7 M^{-1}$, preferably about $10^8 M^{-1}$ to $10^9 M^{-1}$, and more preferably, about $10^{10} M^{-1}$ to $10^{11} M^{-1}$ or higher. A variety of immunoassay formats can be used to determine if antibodies are specifically immunoreactive to a particular peptide. For example, solid-phase ELISA immunoassays are routinely used to select monoclonal antibodies specifically immunoreactive with a peptide. See, e.g., Harlow and Lane (1988) Antibodies, A Laboratory Manual, Cold Spring Harbor Publications, New York, for a description of immunoassay formats and conditions that can be used to determine specific immunoreactivity.

The term "antibody" refers to an immunoglobulin, whether natural or partially or wholly synthetically produced. All derivatives thereof that maintain specific binding ability are also included in the term. The term also covers any protein having a binding domain that is homologous or largely homologous to an immunoglobulin binding domain. An antibody may specifically immunoreactive to a given antigen (e.g., a USP2a peptide of the invention). The term antibody as used herein is intended to include whole antibodies of any isotype (IgG, IgA, IgM, IgE, etc), and fragments thereof. An antibody of the present invention also includes an antibody preparation, e.g., a serum (antiserum). Antibodies can be fragmented using conventional techniques and the fragments screened for utility in the same manner as whole antibodies. Thus, the term includes segments of proteolytically-cleaved or recombinantly-prepared portions of an antibody molecule that selectively reacts with a certain protein or peptide. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. This type of antibodies is produced by the daughter cells of a single antibody-producing hybridoma. A monoclonal antibody typically displays a single binding affinity for any epitope with which it immunoreacts.

The modifier "monoclonal" indicates the character of the antibody as being obtained from a substantially homogeneous population of antibodies, and is not to be construed as requiring production of the antibody by any particular method. Monoclonal antibodies recognize only one type of antigen The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies. The preparation of antibodies, whether monoclonal or polyclonal, is know in the art. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999.

A monoclonal antibody may contain an antibody molecule having a plurality of antibody combining sites, each immunospecific for a different epitope, e.g., a bispecific monoclonal antibody. Monoclonal antibodies may be obtained by methods known to those skilled in the art. Kohler and Milstein (1975), Nature, 256:495-497; U.S. Pat. No. 4,376,110; Ausubel et al. (1987, 1992), eds., Current Protocols in Molecular Biology, Greene Publishing Assoc. and Wiley Interscience, N.Y.; Harlow and Lane (1988), Antibodies: A Laboratory Manual, Cold Spring Harbor Laboratory; Colligan et al. (1992, 1993), eds., Current Protocols in Immunology, Greene Publishing Assoc. and Wiley Interscience, N.Y.; Iyer et al., *Ind. J. Med. Res.*, (2000), 123:561-564.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids. The term nucleic acid is not limited by length, thus encompasses "polynucleotide" and "oligonucleotide." A "nucleic acid encoding a USP2a peptide," as used herein, is preferably between about 6 to about 300 nucleotides in length, more preferably between about 15 to about 150 nucleotides in length, and more preferably, between about 30 to about 90 nucleotides in length, and more preferably, between about 30 to about 60 nucleotides in length As used herein, the term "stringent conditions" refers to conditions where only nucleic acid sequences which are very similar to each other will hybridize. The precise conditions determining the stringency of a particular hybridization include not only the ionic strength, temperature, and the concentration of destabilizing agents such as formamide, but also on factors such as the length of the nucleic acid sequences, their base composition, the percent of mismatched base pairs between the two sequences, and the frequency of occurrence of subsets of the sequences (e.g., small stretches of repeats) within other non-identical sequences. The conditions generally refer to hybridization at either (1) 1×SSC (10×SSC=3 M NaCl, 0.3 M $Na_3$-citrate.$2H_2O$ (88 g/liter), pH to 7.0 with 1 M HCl), 1% SDS (sodium dodecyl sulfate), 0.1-2 mg/ml denatured salmon sperm DNA at 65° C.; (2) 1×SSC, 50% formamide, 1% SDS, 0.1-2 mg/ml denatured salmon sperm DNA at 42° C.; (3) 1% bovine serum albumen (fraction V), 1 mM $Na_2$.EDTA, 0.5 M $NaHPO_4$ (pH 7.2) (1 M $NaHPO_4$=134 g Na$_2$HPO$_4$7H$_2$O, 4 ml 85% H.sub.3PO$_4$ per liter), 7% SDS, 0.1-2 mg/ml denatured salmon sperm DNA at 65° C.; (4) 50% formamide, 5×SSC, 0.02 M Tris-HCl (pH 7.6), 1×Denhardt's solution (100×=10 g Ficoll 400, g polyvinylpyrrolidone, 10 g bovine serum albumin (fraction V), water to 500 ml), 10% dextran sulfate, 1% SDS, 0.1-2 mg/ml denatured salmon sperm DNA at 42° C.; (5) 5×SSC, 5×Denhardt's solution, 1% SDS, 100 [g/ml denatured salmon sperm DNA at 65° C.; or (6) 5×SSC, 5×Denhardt's solution, 50% formamide, 1% SDS, 100 µg/ml denatured salmon sperm DNA at 42° C., with high stringency washes of either (1) 0.3-0.1×SSC, 0.1% SDS at 65° C.; or (2) 1 mM Na$_2$EDTA, 40 mM NaHPO$_4$ (pH 7.2), 1% SDS at 65° C. The above conditions are intended to be used for DNA-DNA hybrids of 50 base pairs or longer. Where the hybrid is believed to be less than 18 base pairs in length, the hybridization and wash temperatures should be 5-10° C. below that of the calculated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6(log$_{10}$ M)+0.41(% G+C)-0.61 (% formamide)-500/L), where "M" is the molarity of monovalent cations (e.g., Na$^+$), and "L" is the length of the hybrid in base pairs.

The term "primer" refers to a nucleic acid which binds to a target nucleic acid of complementary sequence through one or more types of chemical bonds, usually through complementary base pairing, e.g., hydrogen bond formation. As used herein, a primer may include natural (i.e., A, G, C, or T) or a modified base (7-deazaguanosine, inosine, etc.) or a sugar moiety. In addition, the bases in a primer may be joined by a linkage other than a phosphodiester bond, so long as it does not interfere with hybridization. Thus, for example, primers may be peptide nucleic acids in which the constituent bases are joined by peptide bonds rather than phosphodiester linkages. It will be understood by one of skill in the art that primers may bind target sequences lacking complete complementarity with the probe sequence depending upon the stringency of the hybridization conditions. A "probe" is a primer that is directly or indirectly labeled with a detectable label by methods known in the art. The primer is capable of initiating strand elongation. By assaying for the presence, absence, or the level of the probe binding or primer elongation product, one can detect the presence, absence, or the level of the target nucleic acid. Preferably, the probe or primer of the present invention is between about 8 to 100 nucleotides in length, more preferably between about 12 to 50 nucleotides, more preferably between about 12 to 35 nucleotides in length.

As used herein, the term "detectable label" refers to a composition detectable by spectroscopic, photochemical, biochemical, immunochemical, or chemical means. The detectable label can be selected, e.g., from a group consisting of radioisotopes, fluorescent compounds, enzymes, and enzyme co-factors.

The phrase "conservative amino acid substitution" as used herein is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutapolynucleotidesis. The resultant mutants can be screened for biological activity to identify mutants that retain activity.

The term "biomarker" as used herein is a molecule, the level of whose nucleic acid or protein product has a quantitatively differential concentration or level with respect to an aspect of a biological state in a subject. The level of the biomarker can be measured on both the nucleic acid level and the polypeptide level. At the nucleic acid level, a nucleic acid gene or a transcript which is transcribed from any part of the subject's chromosomal and extrachromosomal genome including for example the mitochondrial genome may be measured. Preferably an RNA transcript, more preferably an RNA transcript includes a primary transcript, a spliced transcript, an alternatively spliced transcript, or an mRNA of the biomarker is measured. At the polypeptide level, a prepropeptide, a propeptide, a mature peptide or a secreted peptide of the biomarker may be measured. A biomarker can be used either solely or in conjunction with one or more other identified biomarkers, so as to allow correlation to the biological state of interest as defined herein.

The term "biological state" as used herein to mean the result of the occurrence of a series of biological processes. As the biological processes change relative to each other, the biological state also undergoes changes. One measurement of a biological state, is the level of activity of biologic variables such as biomarkers, parameters, and/or processes at a specified time and under specified experimental or environmental conditions. A biological state can include, for example, the state of an individual cell, an organ, a tissue, and/or a multicellular organism. A biological state can be measured in samples taken from a normal subject or a disease subject. Therefore, measuring the biological state at different time intervals may indicate the state of disease progression in a subject. The term biological state thus includes a state that is indicative of a disease (e.g., diagnosis or diagnosing), a state that is indicative of the progression or regression of a disease (prognosis), a state that is indicative of the susceptibility (risk) of a subject to a disease; and a state that is indicative of the efficacy of a treatment for a disease.

The term biological state is also used herein to refer to clinical signs and diagnostic criteria associated with a disease state. The biological state of a disease state can be quantified with measurements of biological variables. For example, for the disease state of diabetes, the biological variables can include fasting plasma glucose, casual plasma glucose, or oral glucose tolerance test (OGTT) value.

The term "reference pattern of the disease state" is used herein to mean a set of biological variables that are measured in a diseased biological system under specified experimental conditions. For example, the measurements may be performed on blood samples at a specified time following a particular glucose or insulin stimulus.

The term "baseline level or a "control level" of a biomarker expression or activity refers to the level against which biomarker expression in the test sample can be compared.

The term "cancer" in an individual refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an individual, or may circulate in the blood stream as independent cells, such as leukemic cells.

The term "prostate cancer" means a cancer of the prostate tissue.

The phrase "USP2a disease or condition" refers to a disease or disorder in which USP2a is implicated. Examples of USP2a diseases or disorders include, but are not limited to cancers, metabolic syndromes, and the like. Prostate and/or breast cancer are examples of USP2a diseases or conditions.

As used herein, the term "efficacy" refers to either inhibition to some extent, of cell growth causing or contributing to a cell proliferative disorder, or the inhibition, to some extent, of the production of factors (e.g., growth factors) causing or contributing to a cell proliferative disorder. A "therapeutic efficacy" refers to relief of one or more of the symptoms of a cell proliferative disorder. In reference to the treatment of a cancer, a therapeutic efficacy refers to one or more of the following: 1) reduction in the number of cancer cells; 2) reduction in tumor size; 3) inhibition (i.e., slowing to some extent, preferably stopping) of cancer cell infiltration into peripheral organs; 4) inhibition, to some extent, of tumor growth; and/or 5) relieving to some extent one or more of the symptoms associated with the disorder. In reference to the treatment of a cell proliferative disorder other than a cancer, a therapeutic efficacy refers to 1) either inhibition to some extent, of the growth of cells causing the disorder; 2) the inhibition, to some extent, of the production of factors (e.g., growth factors) causing the disorder; and/or 3) relieving to some extent one or more of the symptoms associated with the disorder.

As used herein, the term "sample" or "biological sample" refers to a whole organism or a subset of its tissues, cells or component parts (e.g. body fluids, including but not limited to blood, antiserum, mucus, lymphatic fluid, synovial fluid, cerebrospinal fluid, saliva, amniotic fluid, amniotic cord blood, urine, vaginal fluid and semen). A sample or a biological sample further refers to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. Most often, the sample has been removed from an animal, but the term sample or biological sample can also refer to cells or tissue analyzed in vivo, i.e., without removal from animal. Typically, sample or biological sample will contain cells from the animal, but the term can also refer to non-cellular biological material, such as non-cellular fractions of blood, saliva, or urine, that can be used to measure the cancer-associated polynucleotide or polypeptides levels. A sample or a biological sample further refers to a medium, such as a nutrient broth or gel in which an organism has been propagated, which contains cellular components, such as proteins or nucleic acid molecules.

The term "autologous" means that the sample is obtained from the same subject from which the sample to be evaluated is obtained.

The term "subject" refers to a vertebrate, which is preferably a mammal, more preferably a primate and still more preferably a human. Mammals include, but are not limited to, primates, humans, farm animals, sport animals, and pets.

The term "patient" refers to a subject who requires or is in need of treatment, is receiving treatment, will receive treatment, and/or one who is under care by a medically trained professional for a particular disease or condition.

The term "condition" refers to the status of any cell, organ, organ system or organism. Conditions may reflect a disease state or simply the physiologic presentation or situation of an entity. Conditions may be characterized as phenotypic conditions such as the macroscopic presentation of a disease or genotypic conditions such as the underlying gene or protein expression profiles associated with the condition. Conditions may be benign or malignant.

The term "treating" as used herein, unless otherwise indicated, means reversing, alleviating, inhibiting the progress of, or preventing, either partially or completely, the growth of a disease or condition. The term "treatment" as used herein, unless otherwise indicated, refers to the act of treating.

The term "predicting" means a statement or claim that a particular event will, or is very likely to, occur in the future.

The term "prognosing" means a statement or claim that a particular biologic event will, or is very likely to, occur in the future. Prognosis may also signal a particular outcome of a biological event, e.g., survival times.

The term "progression" means the advancement or worsening of or toward a disease or condition.

The term "cell growth" is principally associated with growth in cell numbers, which occurs by means of cell reproduction (i.e. proliferation) when the rate of the latter is greater than the rate of cell death (e.g. by apoptosis or necrosis), to produce an increase in the size of a population of cells, although a small component of that growth may in certain circumstances be due also to an increase in cell size or cytoplasmic volume of individual cells. An agent that inhibits cell growth can thus do so by either inhibiting proliferation or stimulating cell death, or both, such that the equilibrium between these two opposing processes is altered.

The term "tumor growth" as used herein, unless otherwise indicated, is used as commonly used in oncology, where the term is principally associated with an increased mass or volume of the tumor primarily as a result of tumor cell growth.

The term "carrier" as used herein refers to a diluent, adjuvant, excipient, or vehicle with which an active ingredient, e.g., a nucleic acid, peptide or antibody of the invention is administered. Such carriers can be sterile liquids, such as water and oils.

The phrase a "pharmaceutically acceptable carrier" refers to a non-toxic material that does not interfere with the effectiveness of the biological activity of the active ingredient(s). A pharmaceutically acceptable carrier also refers to molecular entities and compositions that are physiologically tolerable and do not typically produce untoward reactions when administered to a human. Preferably, the term "pharmaceutically acceptable" means approved by a regulatory agency of the Federal or a state government or listed in the U.S. Pharmacopeia or other generally recognized pharmacopeia for use in animals, and more particularly in humans. The characteristics of the carrier will depend on the route of administration. Suitable pharmaceutical carriers are described in "Remington's Pharmaceutical Sciences" by E. W. Martin, 20th Edition.

The term "immunoassay" refers to a test that uses the binding of antibodies to antigens to identify and measure certain substances. Immunoassays often are used to diagnose disease, and test results can provide information about a disease that may help in planning treatment. An immunoassay takes advantage of the specific binding of an antibody to its antigen. Monoclonal antibodies are often used as they usually bind only to one site of a particular molecule, and therefore provide a more specific and accurate test, which is less easily confused by the presence of other molecules. The antibodies used must have a high affinity for the antigen of interest, because a very high proportion of the antigen must bind to the antibody in order to ensure that the assay has adequate sensitivity.

The term "PCR" or "RT-PCR", abbreviates for polymerase chain reaction technologies, as used here refers to technique for the detection or determination of nucleic acid levels, whether synthetic or expressed.

The terms "immunohistochemical" or abbreviated "IHC" as used herein refer to the process of detecting antigens (e.g., proteins) in a biological sample by exploiting the binding properties of antibodies to antigens in said biological sample.

The term "enzyme linked immunosorbent assay" or abbreviated "ELISA" as used herein refers to a technique for the detecting antigens (e.g., proteins) in a biological sample.

The term "radioimmunoassay" or abbreviated "RIA" as used herein refers to a technique for the detecting antigens (e.g. proteins) in a biological sample.

USP2a

The present invention provides USP2a peptides and antibodies specifically immunoreactive to these USP2a peptides. Also provided are nucleic acids encoding the peptides and antibodies of the invention, as well as probes and primers which hybridize to USP2a peptides or proteins. The present invention also provides for methods for using the USP2a peptides and antibodies. The peptides, antibodies, and nucleic acids may be used in researching USP2a-related biological activities, e.g., signal transduction, as well as in disease diagnosis, monitoring, prognosis and therapy.

Isolated USP2a Peptides

The present invention provides isolated USP2a peptides and their variants and/or derivatives, as well as compositions containing two or more USP2a peptides, variants or derivatives.

Preferably, the USP2a peptide of the present invention is or contains an epitope for the production of an antibody specifically immunoreactive to the USP2a peptide.

In a preferred embodiment, the peptide of the present invention comprises a peptide containing or comprising an epitope selected from an immunogenic epitope or an antigenic epitope.

In one embodiment, the USP2a peptide of the invention is synthesized by methods known in the art and as described below. In another preferred embodiment, the USP2a peptide is produced by expressing a nucleic acid encoding the peptide.

USP2a peptides can be synthesized by different methods well known in the art. For example, ribosomally-directed fermentation methods, as well as non-ribosomal strategies and chemical synthesis methods. USP2a peptides containing the 20 natural amino acids can be prepared via recombinant expression systems that utilize the ribosomally directed peptide synthesis machinery of a host organism, e.g., E. coli. Alternatively, USP2a peptides, including those containing unnatural or non-proteninogenic amino acids or modified amino acid side chains can be prepared through a solution-phase chemical synthesis of peptides (e.g., using N-Boc protection and the activated ester route). Protocols for sequence solution-phase chemical synthesis of peptides have been described in Andersson et al., Biopolymers 55:227-250 (2000). One method used for generating peptides is a solution-phase chemical synthesis, which employs a N-tert-butoxy (N-Boc) protected amino acid and a C-protected amino acid (Andersson et al., Biopolymers 55: 227-250 (2000)). An alternative solution-phase method for chemically-catalyzed peptide synthesis employs pre-activated esters as the carboxyl component for coupling (Andersson et al., Biopolymers 55: 227-250 (2000)). In addition, enzyme-mediated solid-phase peptide synthesis has also been employed. Solid-phase peptide synthesis (SPPS) uses insoluble resin supports, and has simplified and accelerated peptide synthesis and facilitated purification (Merrifield, R. B., J. Am. Chem. Soc. 85: 2149-2154 (1963)). Since the growing peptide is anchored on an insoluble resin, unreacted soluble reagents can be removed by simple filtration or washing without manipulative losses. Solid phase peptide synthesis can be performed using automation. Those skilled in the art will recognize that various peptides are within the spirit and scope of the present invention.

In another embodiment, the USP2a peptides of the present invention can be modified, for example, by the addition of an acetyl or amine group or amino acids at the amino- and/or carboxy-terminus of the peptide. Amino acid addition modifications may also be performed, for example, to alter the conformation of the epitope bearing peptide such that the epitope will have a conformation more closely related to the structure of the epitope in the native protein. An example of a modified epitope-bearing peptide of the invention is a peptide in which one or more cysteine residues have been added to the peptide to allow for the formation of a disulfide bond between two cysteines, thus resulting in a stable loop structure of the epitope-bearing peptide under non-reducing conditions. Disulfide bonds can form between a cysteine residue added to the peptide and a cysteine residue of the naturally-occurring epitope, or between two cysteines which have both been added to the naturally-occurring epitope-bearing peptide.

In addition, it is possible to modify one or more amino acid residues of the peptide by substitution with cysteines to promote the formation of disulfide bonded loop structures. Cyclic thioether molecules of synthetic peptides can be routinely generated using techniques known in the art, e.g., as described in PCT publication WO 97/46251, incorporated in its entirety by reference herein. Other modifications of epitope-bearing peptides contemplated by this invention include biotinylation.

In one embodiment, the USP2a peptide of the present invention is modified by adding an acetyl group at the amino terminus and/or an amide group at the carboxyl terminus.

The USP2a peptide of the invention may be provided as a chimeric peptide, such as in the form of a fusion peptide. For instance, the USP2a peptide can be provided as a recombinant fusion peptide which includes a second peptide portion having an amino acid sequence unrelated (heterologous) to the USP2a peptide. For example, the second peptide portion may be glutathione-S-transferase, or a peptide with an enzymatic activity such as alkaline phosphatase, or an epitope tag.

In one embodiment, the USP2a peptide of the present invention has a biological activity, e.g., the ability to bind to a ligand. For example, the USP2a peptide may compete with a USP2a protein in binding to the ligand, thus specifically modulates the activities of the USP2a protein.

In one embodiment, the USP2a peptide contains an amino acid sequence that is identical with or homologous to a sequence represented by either SEQ ID NO. 1 or SEQ ID NO. 2. A homologous sequence is at least 70%, 75%, 80%, 85%, 90%, or 95% identical to the peptide represented by either SEQ ID NO. 1 or SEQ ID NO. 2.

TABLE 1

| USP2a Peptides | | |
|---|---|---|
| Peptide 1 | SEQ ID NO. 1 | LTRPRTYGPSSLLDYDRGRPL |
| Peptide 2 | SEQ ID NO. 2 | GGGK RAESQTRGTE RPLGS |

In a preferred embodiment, the USP2a peptide is encoded by a nucleic acid containing any combination of nucleotide degeneracy. The USP2a peptides of SEQ ID NO. 1 and SEQ ID NO. 2 are derived from highly hydrophilic regions (identified by Kyle-Doolittle plots) of the N-terminal portion of USP2a, and are not present in the isoform USP2b.

The present invention also provides a mixture of two or more USP2a peptides, each containing an amino acid sequence that is identical with or homologous to a sequence comprising SEQ ID NO. 1 or SEQ ID NO. 2. In one embodiment, the mixture contains two or more peptides, each containing an amino acid sequence that is identical with or homologous to a sequence comprising SEQ ID NO. 1 or SEQ ID NO. 2.

The peptides may be derivatized e.g., by conjugation with bovine serum albumin (BSA), or keyhole limpet hemocyanin (KLH), and/or with a functional group such as hydroxy (—OH), acetyl (—CH$_2$COOH) or amide (—NH$_2$).

Antibodies Against USP2a Peptides

In one embodiment, the present invention provides USP2a antibodies that are specifically immunoreactive to peptides, e.g., the USP2a peptides and USP2a proteins, their variants or derivatives as described above. The antibodies may be polyclonal or monoclonal or recombinant, produced by methods known in the art or as described in this application.

In a further embodiment, the antibodies of the present invention may be labeled with a detectable label known by one of skill in the art. The label can be a radioisotope, fluorescent compound, chemiluminescent compound, enzyme, or enzyme co-factor, or any other labels known in the art. In some aspects, the antibody that binds to an entity one wishes to measure (the primary antibody) is not labeled, but is instead detected by binding of a labeled secondary antibody that specifically binds to the primary antibody. Antibodies of the present invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), intracellularly made antibodies (i.e., intrabodies), and epitope-binding fragments of any of the above. The antibodies of the present invention can be from any animal origin including birds and mammals. Preferably, the antibodies are of human, murine (e.g., mouse and rat), donkey, sheep, rabbit, goat, guinea pig, camel, horse, or chicken origin. The antibodies of the present invention can be monospecific or multispecific (e.g., bispecific, trispecific, or of greater multispecificity). Multispecific antibodies can be specific for different epitopes of a peptide of the present invention, or can be specific for both a peptide of the present invention, and a heterologous epitope, such as a heterologous peptide or solid support material. (See, e.g., WO 93/17715; WO 92/08802; WO 91/00360; WO 92/05793; Tutt et al., 1991, J. Immunol., 147:60-69; U.S. Pat. Nos. 4,474,893; 4,714,681; 4,925,648; 5,573,920; 5,601,819; and Kostelny et al., 1992, J. Immunol., 148:1547-1553). For example, the antibodies may be produced against a peptide containing repeated units of a USP2a peptide sequence of the present invention, or they may be produced against a peptide containing two or more USP2a peptide sequences of the present invention, or the combination thereof.

In another embodiment, antibodies can be prepared from any region of the peptides and USP2a peptides of the present invention. In addition, if a polypeptide is a receptor protein, e.g., a receptor USP2a, antibodies can be developed against an entire receptor or portions of the receptor, for example, an intracellular domain, an extracellular domain, the entire transmembrane domain, specific transmembrane segments, any of the intracellular or extracellular loops, or any portions of these regions. Antibodies can also be developed against specific functional sites, such as the site of ligand binding, or sites that are glycosylated, phosphorylated, myristylated, or amidated, for example.

In the present invention, the USP2a peptides for generating antibodies preferably contain a sequence of at least 4, at least 5, at least 6, at least 7, more preferably at least 8, at least 9, at least 10, at least 11, at least 12, at least 13, at least 14, at least 15, and, preferably, between about 5 to about 50 amino acids in length, more preferably between about 10 to about 30 amino acids in length, even more preferably between about 10 to about 20 amino acids in length. The preferred USP2a peptides are those derived from the RTK proteins listed in Table 1 above; that is, preferred USP2a peptides have an amino acid sequence the same as or homologous to a portion of the sequence of the proteins listed in Table 1.

The monoclonal antibodies of the present invention can be prepared using well-established methods known by those skilled in the art. In one embodiment, the monoclonal antibodies are prepared using hybridoma technology, such as those described by Kohler and Milstein (1975), Nature, 256: 495. In a hybridoma method, a mouse, hamster, or other appropriate host animal, is typically immunized with an immunizing agent (e.g., a USP2a peptide of the invention) to elicit lymphocytes that produce or are capable of producing antibodies that will specifically bind to the immunizing agent. Alternatively, the lymphocytes may be immunized in vitro. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-1031. Immortalized cell lines are usually transformed mammalian cells, particularly myeloma cells of rodent, rabbit, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol. (1984), 133:3001; Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies. Preferably, the binding specificity (i.e., specific immunoreactivity) of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known by those skilled in the art. The binding specificity of the monoclonal antibody can, for example, be determined by the Scatchard analysis of Munson and Pollard (1980), Anal. Biochem., 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In another embodiment, the monoclonal antibodies of the present invention can also be made by recombinant DNA methods, such as those described in U.S. Pat. No. 4,816,567, which is hereby incorporated by reference in its entirety. DNA encoding the monoclonal antibodies of the invention can be readily isolated and sequenced using conventional procedures (e.g., by using oligdnucleotide probes that are capable of binding specifically to genes encoding the heavy and light chains of murine antibodies). The hybridoma cells of the invention serve as a preferred source of DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

In another embodiment, polyclonal antibodies of the present invention can also be produced by various procedures known by those skilled in the art. For the production of polyclonal antibodies in vivo, host animals, such as rabbits, rats, mice, sheep, or goats, are immunized with either free or carrier-coupled peptides, for example, by intraperitoneal and/or intradermal injection. Injection material is typically an emulsion containing about 100 μg of peptide or carrier protein. Various adjuvants can also be used to increase the immunological response, depending on the host species. Adjuvants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. Several booster injections may be needed, for instance, at intervals of about two weeks, to provide a useful titer of antibody which can be detected, for example, by ELISA assay using free peptide adsorbed to a solid surface. The titer of antibodies in serum from an immunized animal can be increased by selection of antibodies, e.g., by adsorption of the peptide onto a solid support and elution of the selected antibodies according to methods well known in the art.

Antibodies encompassed by the present invention can also be generated using various phage display methods known by those skilled in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds to the antigen of interest can be selected or identified with antigen, e.g., using labeled antigen or antigen bound or captured onto a solid surface or bead. Phage used in these methods are typically filamentous phage including fd and M13 binding domains expressed from phage with Fab, Fv, or disulfide stabilized antibody domains recombinantly fused to either the phage polynucleotide III or polynucleotide VIII protein. Examples of phage display methods that can be used to make the antibodies of the present invention include those disclosed in Brinkman et al. (1995) J. Immunol. Methods, 182:41-50; Ames et al. (1995) J. Immunol. Methods, 184: 177-186; Kettleborough et al. (1994) Eur. J. Immunol., 24:952-958; Persic et al. (1997) Gene, 187:9-18; Burton et al. (1994) Advances in Immunology, 57:191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108, each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below.

Examples of techniques that can be used to produce antibody fragments such as single-chain Fvs and antibodies include those described in U.S. Pat. Nos. 4,946,778 and 5,258,498; Huston et al. (1991) Methods in Enzymology, 203:46-88; Shu et al. (1993) Proc. Natl. Acad. Sci. USA, 90:7995-7999; and Skerra et al. (1988) Science, 240:1038-1040, each of which is incorporated herein by reference in its entirety.

For some uses, including the in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal immunoglobulin and a human immunoglobulin constant region. Methods for producing chimeric antibodies are known in the art. (See, e.g., Morrison (1985), Science, 229:1202; Oi et al. (1986), BioTechniques, 4:214; Gillies et al. (1989), J. Immunol. Methods, 125:191-202; and U.S. Pat. Nos. 5,807,715; 4,816,567; and 4,816,397, which are incorporated herein by reference in their entirety).

Humanized antibodies are antibody molecules from non-human species that bind to the desired antigen and have one or more complementarity determining regions (CDRs) from the nonhuman species and framework regions from a human immunoglobulin molecule. Often, framework residues in the human framework regions are substituted with corresponding residues from the CDR and framework regions of the donor antibody to alter, preferably improve, antigen binding. These framework substitutions are identified by methods well known in the art, e.g., by modeling of the interactions of the CDR and framework residues to identify framework residues important for antigen binding, and by sequence comparison to identify unusual framework residues at particular positions. (See, e.g., Queen et al., U.S. Pat. Nos. 5,693,762 and 5,585,089; and Riechmann et al. (1988) Nature, 332:323, which are incorporated herein by reference in their entireties). Antibodies can be humanized using a variety of techniques known in the art, including, for example, CDR-grafting (EP 239, 400; PCT publication WO 91/09967; U.S. Pat. Nos. 5,225,539; 5,530,101; and 5,585,089); veneering or resurfacing (EP 592,106; EP 519,596; Padlan (1991), Molecular Immunology, 28 (4/5):489-498; Studnicka et al. (1994) Protein Engineering, 7(6):805-814; Roguska et al. (1994) Proc. Natl. Acad. Sci. USA, 91:969-973; and chain shuffling (U.S. Pat. No. 5,565,332); each of which are incorporated herein by reference in their entirety.

Completely human antibodies are particularly desirable for therapeutic treatment of human patients, so as to avoid or alleviate immune reaction to foreign protein. Human antibodies can be made by a variety of methods known in the art, including the phage display methods described above, using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin polynucleotides. For example, the human heavy and light chain immunoglobulin polynucleotide complexes can be introduced randomly, or by homologous recombination, into mouse embryonic stem cells. Alternatively, the human variable region, constant region, and diversity region may be introduced into mouse embryonic stem cells, in addition to the human heavy and light chain polynucleotides. The mouse heavy and light chain immunoglobulin polynucleotides can be rendered nonfunctional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention.

Thus, using such a technique, it is possible to produce useful human IgG, IgA, IgM, IgD and IgE antibodies. For an overview of the technology for producing human antibodies, see Lonberg and Huszar (1995) Intl. Rev. Immunol., 13:65-93. For a detailed discussion of the technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; 5,939,598; 6,075,181; and 6,114,598, each are incorporated by reference herein in their entirety. In addition, companies such as Abgenix, Inc. (Fremont, Calif.), Protein Design Labs, Inc. (Mountain View, Calif.) and Genpharm (San Jose, Calif.) can be engaged to provide human antibodies directed against a selected antigen using technology similar to the above described technologies.

Once an antibody molecule of the present invention has been produced by an animal, a cell line, chemically synthesized, or recombinantly expressed, it can be purified (i.e., isolated) by any method known in the art for the purification of an immunoglobulin or polypeptide molecule, for example, by chromatography (e.g., ion exchange, affinity, particularly by affinity for the specific antigen, Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

In one embodiment, the present invention provides antibodies that specifically immuoreact to a tyrosine USP2a protein, or fragment or variant thereof.

In one embodiment, the present invention provides a novel monoclonal antibody that specifically recognizes a sequence selected from the group consisting of SEQ ID NO. 1 SEQ ID NO. 2 and variants thereof.

The present invention further provides a mixture containing two or more monoclonal antibodies produced as described above. In a preferred embodiment, the mixture contains two or more monoclonal antibodies raised against different USP2a peptides derived from the same USP2a protein. In another preferred embodiment, the mixture contains two or more monoclonal antibodies raised against different USP2a peptides, at least two of which are derived from different USP2a proteins.

In one embodiment, the antibody mixture contains two or more antibodies raised against peptides containing the amino acid sequence selected from the group consisting of SEQ ID NOs. 1 and 2.

In a preferred embodiment, specifically immunoreactive antibodies include those with a dissociation constant or Kd of less than about $5\times10^{-2}$, $1\times10^{-2}$, $5.times10^{-3}$, $1\times10^{-3}$, $5\times10^{-4}$, or $1\times10^{-4}$. In a more preferred embodiment, specifically immunoreactive antibodies include those with a dissociation constant or Kd less than about $5\times10^{-5}$, $1\times10^{-5}$, $5\times10^{-6}$, $1\times10^{-6}$, $5\times10^{-7}$, $1\times10^{-7}$, $5\times10^{-8}$, or $1\times10^{-8}$. In an even more preferred embodiment, specifically immunoreactive antibodies include those with a dissociation constant or Kd of less than about $5\times10^{-9}$, $1\times10^{-9}$, $5\times10^{-10}$, $1\times10^{-10}$, $5\times10^{-11}$, $10\times10^{-11}$, $5\times10^{-12}$, $1\times10^{-12}$, $5\times10^{-13}$, $1\times10^{-13}$, $5\times10^{-14}$, $1\times10^{-14}$, $5\times10^{-15}$, or $1\times10^{-15}$.

Nucleic Acids

In one embodiment, the present invention provides a nucleic acid encoding a peptide of the present invention, or a complementary sequence thereof.

In another embodiment, the present invention provides a mixture containing two or more nucleic acids as described above. In a further embodiment, the present invention also provides a probe and/or a primer comprising an isolated oligonucleotide, wherein the oligonucleotide comprises a region of nucleotide sequence which hybridizes under stringent conditions to at least 12 consecutive nucleotides of a nucleic acid coding a USP2a peptide of the present invention, or their complementary sequences thereof, or naturally occurring mutants thereof.

In one embodiment, the present invention provides a mixture containing two or more probes and/or primers as described above. In one embodiment, the present invention also provides nucleic acids encoding an antibody of the present invention (including molecules comprising, or alternatively consisting of, antibody fragments or variants thereof). In a specific embodiment, a nucleic acid of the present invention encodes an antibody (including molecules comprising, or alternatively consisting of, antibody fragments or variants thereof), comprising, or alternatively consisting of, a $V_H$ domain having an amino acid sequence of any one of the $V_H$ domains of a heavy chain expressed by an anti-USP2a protein antibody-expressing cell line of the present invention (e.g., a hybridoma) and a $V_L$ domain having an amino acid sequence of a light chain expressed by an anti-USP2a protein antibody-expressing cell line of the present invention. In another embodiment, a nucleic acid molecule of the present invention encodes an antibody (including molecules comprising, or alternatively consisting of, antibody fragments or variants thereof), comprising, or alternatively consisting of, a $V_H$ domain having an amino acid sequence of any one of the $V_H$ domains of a heavy chain expressed by an anti-USP2a protein antibody-expressing cell line of the present invention, or a $V_L$ domain having an amino acid sequence of a light chain expressed by an anti-USP2a protein antibody-expressing cell line of the present invention.

In a further embodiment, two or more nucleic acids encoding an antibody of the present invention may be provided in a mixture. Standard techniques known to those of skill in the art can be used to introduce mutations in the nucleotide sequence encoding a molecule of the present invention, including, for example, site-directed mutapolynucleotidesis and PCR-mediated mutapolynucleotidesis which result in amino acid substitutions. This can be used to prepare desired antibodies, e.g., humanized antibodies as described herein. In a preferred embodiment, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions, relative to the reference $V_H$ domain, $V_H$ CDR1, $V_H$ CDR2, $V_H$ CDR3, $V_L$ domain, $V_L$ CDR1, $V_L$ CDR2, or $V_L$ CDR3. In one embodiment, nucleic acids encoding epitopes can be recombined with a second nucleic acid as an epitope tag (e.g., the hemagglutinin ("HA") tag or flag tag) to aid in detection and purification of the expressed polypeptide. For example, a system for the ready purification of non-denatured fusion proteins expressed in human cell lines has been described by Janknecht et al., (1991, Proc. Natl. Acad. Sci. USA, 88:8972-897). In this system, the second nucleic acid is subcloned into a vaccinia recombination plasmid such that the open reading frame of the polynucleotide is translationally fused to an amino-terminal tag having six histidine residues. The tag serves as a matrix binding domain for the fusion protein. Extracts from cells infected with the recombinant vaccinia virus are loaded onto an Ni.sup.2+ nitriloacetic acid-agarose column and histidine-tagged proteins are selectively eluted with imidazole-containing buffers.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library, or a cDNA library generated from, (or a nucleic acid, preferably poly A+ RNA, isolated from), any tissue or cells expressing the antibody, such as hybridoma cells selected to express an antibody of the invention by PCR amplification using synthetic primers hybridizable to the 3' and 5' ends of the sequence. Alternatively, cloning using an oligonucleotide probe specific for the particular nucleic acid sequence to be identified, e.g., a cDNA clone from a cDNA library that encodes the desired antibody can be employed. Amplified nucleic acids generated by PCR can then be cloned into replicable cloning vectors using any method well known in the art.

Applications

The USP2a peptides, nucleic acids encoding the USP2a peptides, antibodies specifically immunoreactive with the USP2a peptides, as well as nucleic acids of the present invention are useful for research and for disease detection, diagnosis, prognosis and treatment of certain types of cancer, in particular, prostate cancer.

As nonlimiting examples, antibodies of the present invention can be used to purify, detect, and target the USP2a polypeptides of the present invention, including both in vitro and in vivo diagnostic, detection, screening, and/or therapeutic methods. For example, the probes, primers and antibodies can be used in immunoassays for qualitatively and quantitatively measuring levels of USP2a biomarkers in biological samples. (See, e.g., Harlow et al., Antibodies: A Laboratory Manual, Cold Spring Harbor Laboratory Press, 2nd Ed. 1988, which is incorporated by reference herein in its entirety).

In one embodiment, probes, primers and antibodies of the invention can be used as a part of a diagnostic test kit for identifying dysfunctions associated with mis-expression of a USP2a protein containing the sequence of the USP2a peptide of the present invention, such as for detecting in a sample of cells isolated from a patient, a level of a USP2a protein, a level of a nucleic acid encoding a USP2a protein; e.g. measuring a USP2a mRNA level in a cell, or determining whether a genomic USP2a gene has been mutated or deleted. These probes and primers of the present invention can also be used as a part of "antisense" therapy which refers to administration or in situ generation of oligonucleotide probes or their derivatives which specifically hybridize (e.g. bind) under cellular conditions, with the cellular mRNA and/or genomic DNA encoding one or more of the subject USP2a proteins so as to inhibit expression of that protein, e.g. by inhibiting transcription and/or translation. In a further embodiment, the antibodies of the present invention can also be used for therapies as described below.

In one embodiment, the USP2a peptides of the present invention may serve as biomarkers for (1) diagnosis of USP2a related diseases or conditions (e.g., cancers, hyperproliferative conditions, metabolic syndromes, etc) (2) prognosis of diseases (e.g., monitoring disease progression or regression from one biological state to another), (3) determination of susceptibility (risk) of a subject to diseases, or (4) evaluation of the efficacy of a treatment for a disease. Specific biomarkers of the present invention include, but are not limited to, target USP2a peptides, their variants, derivatives or resultant antibodies as described above. In one embodiment, the biological state can be mathematically defined by the values of x and p at a given time, as known in the art. Once a biological state of the model is mathematically specified, numerical integration of the above equation using a computer determines, for example, the time evolution of the biological variables x(t) and hence the evolution of the biological state over time. In a further embodiment, measurements may be performed on biopsy samples, or cell cultures derived from a diseased human or animal. Examples of diseased biological systems include cellular or animal models of the disease or a patient.

In one embodiment, the baseline level can be a "normal level" (i.e., level in a sample from a normal subject). Therefore, it can be determined, based on the control or baseline level of biomarker expression or biological activity, whether a sample to be evaluated for disease cell growth has a measurable increase, decrease, or substantially no change in biomarker expression as compared to the baseline level. In another embodiment, the baseline level can be a "negative control" which herein refers to a baseline level established in a sample from the subject or from a population of individuals which is believed to be normal (i.e., non-tumorous, not undergoing neoplastic transformation, not exhibiting inappropriate cell growth). In another embodiment, a baseline can be indicative of a positive diagnosis of disease. Such a baseline level, also referred to herein as a "positive control" baseline, refers to a level of biomarker expression or biological activity established in a sample from the subject, another subject, or a population of individuals, wherein the sample was believed, based on data for that cell sample, to have the disease (i.e., tumorous, exhibiting inappropriate cell growth, cancerous). In another embodiment, the baseline level can be established from a previous sample of the subject being tested, so that the disease progression or regression of a subject can be monitored over time and/or so that the efficacy of a given therapeutic protocol can be evaluated over time. In a preferred embodiment, the method for establishing a baseline level of the biomarker expression is selected based on the sample type, the tissue or organ from which the sample is obtained, the status of the subject to be evaluated, and, as discussed above, the focus or goal of the assay (e.g., diagnosis, staging, monitoring). In a more preferred embodiment, the method is the same method that will be used to evaluate the sample in the subject. In a most preferred embodiment, the baseline level is established using the same cell type as the cell to be evaluated.

In one embodiment, the baseline level of biomarker expression or biological activity is established in an autologous control sample obtained from the subject. The autologous control sample can be a sample of isolated cells, a tissue sample or a bodily fluid sample, and is preferably a cell sample or tissue sample. In a further embodiment, the control sample should be of or from the same cell type. In a preferred embodiment, the control sample is obtained from the same organ, tissue or bodily fluid as the sample to be evaluated, such that the control sample serves as the best possible baseline for the sample to be evaluated. In one embodiment, when the goal of the assay is diagnosis of abnormal cell growth, it is desirable to take the control sample from a population of cells, a tissue or a bodily fluid which is believed to represent a normal cell, tissue, or bodily fluid, or at a minimum, a cell or tissue which is least likely to be undergoing or potentially be predisposed to develop tumor cell growth. For example, if the sample to be evaluated is an area of apparently abnormal cell growth, such as a tumorous mass, the control sample is preferably obtained from a section of apparently normal tissue (i.e., an area other than and preferably a reasonable distance from the tumorous mass) in the tissue or organ where the tumorous mass is growing. In one aspect, if a tumor to be evaluated is in the colon, the test sample would be obtained from the suspected tumor mass in the colon and the control sample would be obtained from a different section of the colon, which is separate from the area where the mass is located and which does not show signs of uncontrolled cellular proliferation.

In one embodiment, a difference in expression level between a test sample and a baseline, either measured at the nucleic acid or the peptide level, is considered positive for the particular purpose of the test if the difference is at least 20%, 30%, 40%, 50%, preferably at least 70%, more preferably 80%, 90%, or even more preferably 2-fold, 3-fold, 4-fold, 5-fold, 10-fold or more. In one embodiment, target USP2a biomarkers may originate from different parts of the cell and may be cell surface receptors, although they can also be intracellular proteins. The USP2a proteins may be over expressed or under expressed in a sample. The level of the target gene or protein can be determined by conventional methods such as expression assays to determine the level of expression of the gene, by biochemical assays to determine the level of the gene product, or by immunoassays using antibodies reactive to USP2a. Examples of detection methods include those known to those of skill in the art or taught in numerous texts and laboratory manuals (see for example, Ausubel et al. (1995) Short Protocols in Molecular Biology, 3rd Ed. John Wiley & Sons, Inc.). If appropriate, the target USP2a can be identified as a cell surface molecule in tissue or in a bodily fluid, such as serum.

For example, methods of detecting nucleic acid of a USP2a biomarker include but are not limited to, RNA fingerprinting, Northern blotting, polymerase chain reaction (PCR), ligase chain reaction, Q beta replicase, isothermal amplification method, strand displacement amplification, transcription based amplification systems, nuclease protection (SI nuclease or RNAse protection assays) as well as methods disclosed in WO88/10315, WO89/06700, PCT/US87/00880, PCT/US89/01025; all of which are incorporated herein by reference.

In one embodiment, detecting the expression level of a nucleic acid of a USP2a biomarker may include (i) providing a probe or a primer of the present invention; (ii) contacting the probe or the primer with a sample; and (iii) detecting, by hybridization of the probe or the primer to nucleic acids in the sample, the presence and absence or the level of a USP2a biomarker nucleic acid. The method may also include amplifying the nucleic acid of the USP2a biomarker before detecting. For instance, the probe or the primer can be employed in a polymerase chain reaction (PCR) or in a ligation chain reaction (LCR). A difference in the level of expression between a test sample (e.g., from a patient subject) and a control sample (e.g., from a normal subject) is indicative of the biological state of interest. The probe or the primer used may also be a mixture of two or more probes or primers as described above.

In a further embodiment, the nucleic acid detection method also includes detecting, in a sample of the subject, the presence or absence of a genetic lesion spanning a region represented by a nucleic acid encoding a USP2a peptide of the present invention. Detecting the genetic lesion includes ascertaining the existence of at least one of (i) deletion of one or more nucleotides from a USP2a gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of a USP2a protein.

In alternate embodiments, the level of a USP2a protein is detected in an immunoassay using an antibody of the present invention, which is specifically immunoreactive with the USP2a protein. Preferably, the method of detection comprises contacting the sample with an antibody of the present invention (including an antibody mixture) and determining the presence and absence or the level of a USP2a biomarker protein. A difference in the level of expression between a test sample (e.g., from a patient subject) and a control sample (e.g., from a normal subject) is indicative of the biological state of interest. The antibody used may also be a mixture of two or more antibodies, or antibodies raised against a mixture of USP2a peptides as described above.

Various methods known in the art for detecting specific antibody-antigen binding can be used. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). Zola, Monoclonal Antibodies: A Manual of Techniques, pp. 147-158 (CRC Press, Inc. 1987). In one embodiment, a detectable label can be attached to the subject antibodies and is selected so as to meet the needs of various uses of the method which are often dictated by the availability of assay equipment and compatible immunoassay procedures. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or .beta.-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). General techniques to be used in performing the various immunoassays noted above are known to those of ordinary skill in the art.

In another embodiment of the invention, an antibody of the present invention (i.e., the primary antibody) needs not be labeled, and the presence thereof can be detected using a labeled second antibody which binds to the primary antibody.

In one embodiment, antibodies can be arrayed on a substrate and detection of biomarkers may be performed by antibody array method, for example, as described in an application by the same inventor entitled "Antibody Protein Analysis Chip," hereby incorporated by reference in its entirety.

In another embodiment, the antibodies can be used for in vivo diagnostic assays, such as in vivo imaging. Generally, the antibody is labeled with a radionuclide (such as $^{111}$In, $^{99}$Tc, $^{14}$C, $^{131}$I, $^{125}$I, or $^{3}$H) so that the cells or tissue of interest can be localized using immunoscintiography. In a further embodiment, the antibody may also be used as staining reagent in pathology, following techniques well known in the art.

One embodiment of the present invention is a method for the diagnosis of a cancer that includes determining the level of USP2a in a test sample. In this method, the level of USP2a is indicative of the presence of cancer cells. The presence of USP2a at an increased level as compared to a normal baseline control is an indication of the presence of a cancer, a possible predisposition to such cancer or a susceptibility to an anticancer therapeutic treatment. The level of USP2a can be determined by conventional methods such as expression assays to determine the level of expression of the USP2a gene (using the probes/primers, or mixtures thereof provided by the invention), by biochemical assays to determine the level of the gene product, or by immunoassays. In one embodiment of this method, the level of USP2a can be determined by identifying USP2a as a cell surface molecule in tissue or by detecting USP2a in soluble form in a bodily fluid, such as serum, that can be immobilized. The USP2a level can be determined by contacting a patient test sample with an antibody, or a fragment thereof, that binds specifically to USP2a and determining whether the anti-USP2a antibody or fragment has bound to the USP2a protein. The USP2a level can be determined by using a first monoclonal antibody that binds specifically to USP2a and a second antibody that binds to the first antibody. This method can be used to determine the prognosis for cancer in the patient or to determine the susceptibility of the patient to a therapeutic treatment.

A further embodiment of the present invention is a method for the diagnosis of a tumor or the monitoring of tumor growth or regression or tumor therapy in a patient. The methods include determining the level of USP2a in a patient sample.

In one embodiment, the present invention further provides kits for disease diagnosis, prognosis, risk assessment, and/or treatment efficacy determination. Such kits are useful in a clinical setting for use in diagnosing a patient for a disease, monitoring the disease progression, testing patient's samples (e.g., biopsied), for example, to determine or predict if the patient's disease (e.g., cancer) will be resistant or sensitive to a given treatment or therapy with a drug, compound, chemotherapy agent, or biological treatment agent. In a further embodiment, the kit also provides a predictor set comprising a nucleic acid or a nucleic acid mixture of the present invention or an antibody or an antibody mixture of the present invention. In another embodiment, the kits may encompass desired reagents for the specific detection method to be used, e.g., nucleic acid assays and immunoassays as described above, and known in the art.

In a preferred embodiment, the kit preferably contains any means of detecting the expression or activity of USP2a in a test sample, and preferably includes a probe, PCR primers, or a mixture of nucleic acids of the invention, or an antibody, a mixture of antibodies of the invention, antigen binding peptide, or fragment thereof, that binds to USP2a. The kit can include any reagent needed to perform a diagnostic method envisioned herein. The antibody, or fragment thereof, can be conjugated to another unit, for example a marker or immobilized to a solid carrier (substrate). In a further embodiment, the kit can contain a second antibody for the detection of USP2a:antibody complexes. In one embodiment, the kit can contain a means for detecting a control marker characteristic of a cell type in the test sample. The antibody, or fragment thereof, may be present in free form or immobilized to a substrate such as a plastic dish, a test tube, a test rod and so on. The kit can also include suitable reagents for the detection of and/or for the labeling of positive or negative controls, wash solutions, dilution buffers and the like, as well as instructions.

More specifically, according to the present invention, a means for detecting USP2a expression or biological activity can be any suitable reagent that can be used in a method for detection of USP2a expression or biological activity as described previously herein. Such reagents include, but are not limited to: a probe or primer, or a mixture of nucleic acids of the invention, that hybridizes under stringent hybridization conditions to USP2a or a fragment thereof (including to a USP2a-specific regulatory region in the biomarker-encoding gene); RT-PCR primers for amplification of mRNA encoding USP2a or a fragment thereof; and/or an antibody or a mixture of antibodies of the present invention, antigen-binding fragment thereof or other antigen-binding peptide that selectively binds to USP2a.

In another embodiment, the means for detecting a USP2a marker and/or a control marker of the assay kit of the present invention can be conjugated to a detectable tag or detectable label. Such tag can be any suitable tag which allows for detection of the reagents used to detect USP2a or control marker and includes, but is not limited to, any composition or label detectable by spectroscopic, photochemical, biochemical, immunochemical, electrical, optical or chemical means, as described herein and known in the art.

In a further embodiment, the means for detecting the assay kit of the present invention can be immobilized on a substrate. Such a substrate can include any suitable substrate for immobilization of a detection reagent such as would be used in any of the previously described methods of detection. Briefly, a substrate suitable for immobilization of a means for detecting includes any solid support, such as any solid organic, biopolymer or inorganic support that can form a bond with the means for detecting without significantly effecting the activity and/ or ability of the detection means to detect the desired target molecule. Exemplary organic solid supports include, but are not limited to, polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include, but are not limited to, cellulose, polydextrans (e.g., Sephadex), agarose, collagen and chitin. Exemplary inorganic supports include, but are not limited to, glass beads (porous and nonporous), stainless steel, metal oxides (e.g., porous ceramics such as $ZrO_2$, $TiO_2$, $Al_2O_3$, and NiO) and sand.

Other Applications

In one embodiment, the present invention provides a method for modulating one or more of growth, differentiation, or survival of a cell by modulating USP2a expression or activity, e.g., by potentiating or disrupting certain protein-protein interactions. In general, whether carried out in vivo, in vitro, or in situ, the method comprises treating the cell with an effective amount of a USP2a peptide, a nucleic acid, or an antibody of the present invention, at least one of (i) rate of growth, (ii) differentiation, or (iii) survival of the cell. The modulatory effects as described herein are useful for researchers on signal transduction pathways, as well as disease treatment.

In another embodiment, the present invention provides an antisense nucleic acid that specifically hybridizes to a nucleic acid encoding USP2a of the present invention, wherein the antisense nucleic acid inhibits the expression of USP2a. In a further embodiment, the present invention provides a method of inhibiting the expression of USP2a of the present invention by contacting a sample in vitro, or in vivo, with an antisense nucleic acid of the present invention so that expression of USP2a is inhibited.

In another embodiment, an antibody of the present invention may bind to and competitively inhibit polypeptide multimerization and/or binding of USP2a of the present invention to a ligand, thus modulate the activity of USP2a in signal transduction.

In one embodiment, a USP2a MAb, upon binding to the corresponding USP2a protein or peptide located on a cell membrane, induces apoptosis in the cell expressing the corresponding USP2a on its membrane. The MAb may also reduce the number of cells, or inhibit cell growth of the cells that express corresponding USP2a (known as USP2a-expressing cells). In a preferred embodiment, the reduction in cell number or inhibition of cell growth is by at least about 10%, about 20%, about 30%, about 40%, about 50%, about 65%, about 75%, or greater. In another embodiment, the USP2a-expressing cells are disease cells, e.g., cancer or tumor cells. In a more preferred embodiment, the cancers include but are not limited to, colorectal cancer, pancreatic cancer, lung cancer, gastric cancer, hepatocellular carcinoma, breast cancer and thyroid cancer.

In one embodiment, the MAb may also inhibit the proliferation of USP2a-expressing cells, preferably by at least about 10%, about 20%, about 30%, about 40%, about 50%, about 65%, about 75%, or greater. In another embodiment, the MAb inhibits the cell growth of the USP2A-expressing cells, preferably by at least about 10%, about 20%, about 30%, about 40%, about 50%, about 65%, about 75%, or greater. Preferably, the USP2a-expressing cells are disease cells, e.g., cancer or tumor cells. More preferably, the cancers include but are not limited to, colorectal cancer, pancreatic cancer, lung cancer, gastric cancer, hepatocellular carcinoma, breast cancer and thyroid cancer.

Therefore, antibodies of the present invention can act as agonists or antagonists of USP2a. For example, the present invention includes antibodies which disrupt receptor/ligand interactions with polypeptides of the present invention either partially or fully. The present invention also includes receptor-specific antibodies which do not prevent ligand binding, but do prevent receptor activation. Receptor activation (i.e., signaling) can be determined by techniques described herein or as otherwise known in the art. For example, receptor activation can be determined by detecting the phosphorylation (e.g., on tyrosine or serine/threonine) of the receptor or its substrate by immunoprecipitation followed by Western Blot analysis.

In one embodiment, the method can be carried out with USP2a therapeutics such as a monoclonal antibody, an antisense nucleic acid, or a USP2a peptide of the present invention which agonizes or antagonizes the effects of signaling from a USP2a protein or ligand binding of a USP2a protein. The antisense nucleic acid of the present invention inhibits the expression of a target USP2a gene, while the peptide or the antibody may competitively inhibit ligand interactions with the wild-type USP2a protein.

In a further embodiment, the USP2a peptides of the present invention can be introduced together with a carrier protein, such as an albumin, to an animal system (such as rabbit or mouse). Alternatively, if the peptide is of sufficient length (e.g., at least about 15-25 amino acids), the polypeptide can be presented without a carrier.

In one embodiment, the composition for therapy is formulated for administration by intraperitoneal, intravenous, subcutaneous, and intramuscular injections, and other forms of administration such as oral, mucosal, via inhalation, sublingually, etc.

In one embodiment, the nucleic acids and antibodies of the present invention may be delivered with a carrier. Water or aqueous solution, saline solutions and aqueous dextrose and glycerol solutions are preferably employed as carriers, particularly for injectable solutions. The carrier may also be a pharmaceutically acceptable carrier.

In another embodiment, a nucleic acid encoding any of the antibodies of the present invention can also be used for delivery and expression of any of the antibodies of the present invention in a desired cell. It is apparent that an expression vector can be used to direct expression of an antibody. The expression vector can be administered by any means known in the art, such as, but not limited to, intraperitoneally, intravenously, intramuscularly, subcutaneously, intrathecally, intraventricularly, orally, enterally, parenterally, intranasally, dermally, sublingually, or by inhalation. For example, administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471; each of which is incorporated by reference in its entirety.

The therapeutic polynucleotides and polypeptides of the present invention can be delivered using gene delivery vehicles. The gene delivery vehicle can be of viral or non-viral origin (see generally, Jolly (1994), Cancer Gene Therapy 1:51; Kimura (1994), Human Gene Therapy 5:845; Connelly (1985), Human Gene Therapy 1:185; and Kaplitt (1994), Nature Genetics 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses, e.g., PCT Publication Nos. WO 90/07936; WO 94/03622; WO 93/25698; WO 93/25234; WO 93/11230; WO 93/10218; WO 91/02805; U.S. Pat. Nos. 5,219,740; 4,777,127; GB Patent No. 2,200,651; and EP Patent No. 0 345 242; alphavirus-based vectors, e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors, e.g., PCT Publication Nos. WO 94/12649, WO 93/03769; WO 93/19191; WO 94/28938; WO 95/11984 and WO 95/00655; each of which is incorporated by reference in its entirety. Administration of DNA linked to killed adenovirus as described in Curiel (1992), Hum. Gene Ther. 3:147 can also be employed.

Non-viral delivery vehicles and methods can also be employed, including, but are not limited to, polycationic condensed DNA linked or unlinked to killed adenovirus alone (see, e.g., Curiel (1992), Hum. Gene Ther. 3:147); ligand-linked DNA (see, e.g., Wu (1989), J. Biol. Chem. 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859 herein incorporated by reference in their entirety. Liposomes that can act as gene delivery vehicles are described in U.S. Pat. No. 5,422,120; PCT Publication Nos. WO 95/13796; WO 94/23697; WO 91/14445; and EP Patent NO. 0 524 968 herein incorporated in their entirety. Additional approaches are described in Philip (1994), Mol. Cell. Biol. 14:2411 and in Woffendin (1994), Proc. Natl. Acad. Sci. 91:1581.

Other formulations include suitable delivery forms known in the art including, but not limited to, carriers such as liposomes. See, for example, Mahato et al. (1997) Pharm. Res. 14:853-859. Liposomal preparations include, but are not limited to, cytofectins, multilamellar vesicles and unilamellar vesicles.

In another embodiment, the present invention also contemplates administration of a composition comprising nucleic acids or antibodies of the present invention conjugated to other molecules, such as detectable labels, or therapeutic or cytotoxic agents. The agents may include, but are not limited to radioisotopes, toxins, toxoids, inflammatory agents, enzymes, antisense molecules, peptides, cytokines, or chemotherapeutic agents. Methods of conjugating the antibodies with such molecules are generally known to those of skilled in the art. See, e.g., PCT publications WO 92/08495; WO 91/14438; WO 89/12624; U.S. Pat. No. 5,314,995; and EP 396,387; the disclosures of which are incorporated herein by reference in their entirety.

The dosage required for the treatment depends on the choice of the route of administration, the nature of the formulation, the nature of the subject's illness, the subject's size, weight, surface area, age and sex; other drugs being administered, and the judgment of the attending physician. Suitable dosages are in the range of 0.01-1000.0 mg/kg.

The practice of the present invention will employ, unless otherwise indicated, conventional techniques of cell biology, cell culture, molecular biology, microbiology, recombinant DNA, and immunology, which are within the skill of the art.

Such techniques are explained fully in the literature and herein above. See, for example, Molecular Cloning A Laboratory Manual, 2nd Ed., ed. by Sambrook, Fritsch and Maniatis (Cold Spring Harbor Laboratory Press: 1989); DNA Cloning, Volumes 1 and 11 (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. 1. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

The invention will be better understood by reference to the following example which serve to illustrate but not to limit the present invention.

EXAMPLES

Example 1

Production and Characterization of Polyclonal Antisera for USP2a

SPF rabbits (Maine Biotechnology Services, Inc.) were used to generate polyclonal antisera. Forty eight (48) rabbits were used. The polyclonal antibodies are referred to hereinafter as USP2a-1 and USP2a-2.

Each rabbit was injected with one of the peptides of the present invention as shown in Table 2.

TABLE 2

| Injected Peptides | |
|---|---|
| USP2a-1 (SEQ ID NO. 1) | LTRPRTYGPSSLLDYDRGRPL |
| USP2a-2 (SEQ ID NO. 2) | GGGK RAESQTRGTE RPLGS |

The rabbits were bled, and the resulting antisera were then pooled and affinity purified using the same epitopes against which they had been raised. Affinity purification was carried out according to the following procedure:
Step 1: Affinity Column Preparation
The immunoaffinity column was prepared by coupling the peptides of SEQ ID NO. 1 or SEQ ID NO. 2 to 1 ml of activated sepharose beads.
Step 2: Loading of the Antisera
The antisera was loaded at a concentration of 2 μg/mL onto the peptide-sepharose column and incubated 1 hour at 37° C.
Step 3: Elution
After several washes of the column, the elution of bound antibody was performed using elution buffer containing 0.02% sodium azide. Fractions containing the antibody were pooled and the final concentration of immunopurified antibody was determined by reading the optical density at 280 nm using U.V. spectrophotometer.
Step 4: ELISA Test of the Immunopurified Antibody
The blocking reagent SeaBlock was loaded into the wells in a NEAT concentration and incubated for 30 minutes at 37° C. After the incubation, four samples of serum (pre-bleed Rb 1, pre-bleed Rb 2, peptide 1 and peptide 2) were added into the wells at 6 different concentrations. The four samples were diluted using 0.15M PBS to concentrations of 1:50, 1:250, 1:1250, 1:6250, 1:31250, and 1:156000. Each of these concentrations of the four serums were added to the wells then incubated at room temperature for 30 minutes. Lastly, a secondary antibody, anti-Rb HRP, (HRP-lot #86569) was diluted to a concentration of 1:10000 using 0.15M PBS with 0.05% Tween20 and incubated at room temperature for 30 minutes. The final concentration of the samples, as shown in Tables 3 and 4, was determined by reading the absorbance at 450 nm using the U.V. spectrophotometer.

TABLE 3

Pre-Bleed Rb 1 and 2 Sample Analysis

| Concentration | ELISA Reactivity to Antisera Rb1 | ELISA Reactivity to Antisera Rb2 |
| --- | --- | --- |
| 1:50 | 0.33 | 0.34 |
| 1:250 | 0.24 | 0.02 |
| 1:1250 | 0.36 | 0.03 |
| 1:6250 | 0.33 | 0.01 |
| 1:31250 | 0.20 | 0.20 |
| 1:156000 | 0.43 | 0.13 |

TABLE 4

USP2a-1 Sample Analysis

| Concentration | ELISA Reactivity to Antisera USP2a Peptide 1 | ELISA Reactivity to Antisera USP2a Peptide 2 |
| --- | --- | --- |
| 1:50 | 0.79 | 0.87 |
| 1:250 | 0.58 | 0.58 |
| 1:1250 | 0.94 | 0.85 |
| 1:6250 | 0.93 | 0.63 |
| 1:31250 | 0.86 | 0.95 |
| 1:156000 | 0.64 | 0.53 |

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method for staging or monitoring the progression of a disease associated with increased USP2a level in a subject which has said disease, the method comprising:
   a) obtaining a sample from the subject;
   b) contacting the sample with an anti-USP2a antibody mixture consisting of isolated antibodies that are specifically reactive with a USP2a peptide consisting of the amino acid sequence of SEQ ID NO. 1, or variants thereof, and isolated antibodies that are specifically reactive with a USP2a peptide consisting of the amino acid sequence of SEQ ID NO. 2, or variants thereof;
   c) determining a level of USP2a protein in the sample detected by said antibody mixture in an immunoassay; and
   d) comparing the level of the USP2a protein in the sample to a positive control baseline level of the USP2a protein, wherein a difference in the level of USP2a protein in the sample as compared to the positive control baseline level of greater than 20% overexpression is indicative of the stage or progression of said disease in the subject.

2. The method of claim 1, wherein both said isolated antibodies are labeled with a detectable label.

3. The method of claim 2, wherein the immunoassay for determining the level of USP2a protein is selected from the group consisting of immunoblot, enzyme-linked immunosorbant assay (ELISA), radioimmunoassay (RIA), immunoprecipitation, immunohistochemistry and immunofluorescence.

4. The method of claim 1, wherein said disease is prostate cancer.

5. The method of claim 1, wherein the positive control baseline level of USP2a is the level of USP2a protein in a previous sample from said subject.

* * * * *